United States Patent
Zicari et al.

(10) Patent No.: US 10,610,492 B2
(45) Date of Patent: Apr. 7, 2020

(54) SPRAY DRY METHOD FOR ENCAPSULATION OF BIOLOGICAL MOIETIES AND CHEMICALS IN POLYMERS CROSS-LINKED BY MULTIVALENT IONS FOR CONTROLLED RELEASE APPLICATIONS

(71) Applicant: THE REGENTS OF THE UNIVERSITY OF CALIFORNIA, Oakland, CA (US)

(72) Inventors: Tina Jeoh Zicari, Davis, CA (US); Herbert B. Scher, Moraga, CA (US); Monica C. Santa-Maria, Davis, CA (US); Scott Strobel, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 149 days.

(21) Appl. No.: 15/615,520

(22) Filed: Jun. 6, 2017

(65) Prior Publication Data
US 2017/0333360 A1 Nov. 23, 2017

Related U.S. Application Data

(60) Division of application No. 14/288,110, filed on May 27, 2014, now Pat. No. 9,700,519, which is a continuation of application No. PCT/US2012/071447, filed on Dec. 21, 2012.

(60) Provisional application No. 61/579,893, filed on Dec. 23, 2011.

(51) Int. Cl.
| | |
|---|---|
| *A61K 9/50* | (2006.01) |
| *A61K 38/38* | (2006.01) |
| *A61K 38/47* | (2006.01) |
| *A61K 47/30* | (2006.01) |
| *C08J 3/12* | (2006.01) |
| *B01J 13/04* | (2006.01) |
| *C08J 3/24* | (2006.01) |
| *A61K 9/16* | (2006.01) |

(52) U.S. Cl.
CPC .......... *A61K 9/5036* (2013.01); *A61K 9/5089* (2013.01); *A61K 38/385* (2013.01); *A61K 38/47* (2013.01); *A61K 47/30* (2013.01); *B01J 13/043* (2013.01); *B01J 13/046* (2013.01); *C08J 3/122* (2013.01); *C08J 3/24* (2013.01); *A61K 9/1694* (2013.01); *C08J 2305/04* (2013.01); *C08J 2305/06* (2013.01); *C08J 2389/00* (2013.01); *C12Y 302/01004* (2013.01); *C12Y 302/01008* (2013.01)

(58) Field of Classification Search
None
See application file for complete search history.

(56) References Cited

U.S. PATENT DOCUMENTS

| | | | |
|---|---|---|---|
| 3,655,129 | A | 4/1972 | Seiner |
| 4,064,294 | A | 12/1977 | Babil |
| 5,492,646 | A | 2/1996 | Langley |
| 2004/0219208 | A1 | 11/2004 | Kawamura |
| 2006/0110306 | A1 | 5/2006 | Chow |
| 2008/0138420 | A1 | 6/2008 | Speaker |
| 2010/0166874 | A1 | 7/2010 | Malakhov |
| 2011/0008293 | A1 | 1/2011 | Bhandari |

OTHER PUBLICATIONS

Erdinc, B.I. 2007. Micro/nanoencapsulation of proteins within alginate/chitosan matrix by spray drying. Master of Science. Dept. of Chem. Eng. Queen's University, Ontario, Canada, pp. 1-90. Retrieved from the internet: <https://www.mobt3ath.com/uplode/book/book-12812.pdf> specif. pp. 12, 13, 36, 44, 45, 46, 48.*
Crow, B.B. et al., "Release of Bovine Serum Albumin from a Hydrogel-Cored Biodegradable Polymer Fiber", Biopolymers 81:419-427, published online Jan. 17, 2006.
Bodmeier, Roland, "A Novel Approach to the Oral Delivery of Micro- or Nanoparticles", Pharmaceutical Research 6(5): 413-417, 1989.
Reis, Catarina P. et al., "Review and current status of emulsion/dispersion technology using an internal gelation process design of alginate particles", Journal of Microencapsulation 23(3): 245-257, 2006.
United States Patent and Trademark Office (USPTO), International Search Report and Written Opinion dated Mar. 5, 2013, counterpart PCT InternationalApplication No. PCT/US2012/071447, pp. 1-9, with claims searched, pp. 10-13.
Santa-Maria, Monica et al., "Microencapsulation of bioactives in cross-linked alginate matrices by spray drying" Journal of Microencapsulation, 2012, pp. 1-10.

(Continued)

*Primary Examiner* — Renee Claytor
*Assistant Examiner* — Sharon M. Papciak
(74) *Attorney, Agent, or Firm* — O'Banion & Ritchey LLP; John P. O'Banion

(57) ABSTRACT

Microencapsulation of bioactive and chemical cargo in a stable, cross-linked polymer matrix is presented that results in small particle sizes and is easily scaled-up for industrial applications. A formulation of a salt of an acid soluble multivalent ion, an acid neutralized with a volatile base and one or more monomers that cross-link in the presence of multivalent ions is atomized into droplets. Cross-linking is achieved upon atomization where the volatile base is vaporized resulting in a reduction of the pH of the formulation and the temporal release of multivalent ions from the salt that cross-link the monomers forming a capsule. The incorporation of additional polymers or hydrophobic compounds in the formulation allows control of hydration properties of the particles to control the release of the encapsulated compounds. The operational parameters can also be controlled to affect capsule properties such as particle-size and particle-size distribution.

7 Claims, 5 Drawing Sheets

(56) References Cited

OTHER PUBLICATIONS

Nicodemus, Garret D. et al., "Cell Encapsulation in Biodegradable Hydrogels for Tissue Engineering Applications" Tissue Engineering: Part B, vol. 4, No. 2, (2008) pp. 1-18.

Omidian, H. et al., "Pharmaceutical Polymers" in "Martin's Physical Pharmacy and Pharmaceutical Sciences", 6th Edition, Chapter 20; P Sinko (Ed); Lippincott Williams & Wilkins (publisher), pp. 492-515, 2010.

Kwok, K. Keith et al., "Production of 5-15um Diameter Alginate-Polylysine Microcapsules by an Air-Atomization Technique", Pharmaceutical Research 8(3): 341-344, 1991.

Papciak, Sharon M., Knovel Solvents—A Properties Database. Ammonia. Datasheet [online]. [retrieved on Apr. 13, 2016]. Copyright 2008 ChemTec Publishing. Retrieved from the Internet: <URL: https://app.knovel.com/web/view/html/ . . . see NPL for full URL citation. pp. 1-2.

Brown et al., "Factors that affect solubility", In: Chemistry: The Central Science, 13th ed. Copyright 2015 Pearson Education publishing as Prentice Hall. Brown, LeMay, Bursten, Murphy, Woodward, and Stoltzfus, pp. 1-8.

* cited by examiner

SPRAY DRY METHOD FOR ENCAPSULATION OF BIOLOGICAL MOIETIES AND CHEMICALS IN POLYMERS CROSS-LINKED BY MULTIVALENT IONS FOR CONTROLLED RELEASE APPLICATIONS

This application is a division of U.S. patent application Ser. No. 14/288,110 filed on May 27, 2014, incorporated herein by reference in its entirety, which is a 35 U.S.C. § 111(a) continuation of PCT international application number PCT/US2012/071447 filed on Dec. 21, 2012, incorporated herein by reference in its entirety, which claims priority to, and the benefit of, U.S. provisional patent application Ser. No. 61/579,893 filed on Dec. 23, 2011, incorporated herein by reference in its entirety. Priority is claimed to each of the foregoing applications.

The above-referenced PCT international application was published as PCT International Publication No. WO 2013/096883 on Jun. 27, 2013, and is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND OF THE INVENTION

1. Field of Invention

This invention pertains generally to the production and use of microcapsules and more particularly to a method for producing small cross-linked microcapsules in a single step by spray drying, wherein polymer gelation occurs during spray drying upon volatilization of a base and rapid release of otherwise unavailable multivalent ions as the pH is reduced. A range of small to large microcapsules can be produced.

2. Background

Encapsulation of bioactive moieties is a common practice in the food, biotechnology and pharmaceutical industries to increase the stability and shelf life of the encapsulated compound and to control its delivery. In general, the encapsulation matrix confers a protective layer against adverse environmental conditions and regulates the release of the encapsulated compound in the target application.

Polymers are typically used as the encapsulating medium which allows cross-linking between the molecules to improve overall stability of the encapsulated product. One example is the use of a charged polymer as the encapsulation matrix such that multiple polymers are cross-linked via electrostatic interactions with multivalent ions. This form of ion-mediated cross-linking occurs spontaneously upon contact between polymer and ions, and rapidly converts a low-viscosity solution to a gelled mass.

Among encapsulation materials, alginates are preferred because of being non-toxic, biocompatible and relatively inexpensive. Alginic acids (alginates) are negatively charged polysaccharides readily cross-linked by divalent calcium ions and ubiquitously utilized in biotechnology and food applications. Chemically, alginates are linear copolymers of [1→4] linked β-D-mannuronic acid (M) and α-L-guluronic acid (G), arranged as blocks of either type or as a random distribution of each type. They are generally obtained from marine brown algae and have varied chemical structure and composition depending on the source and harvesting season. An important property of alginates is that they can selectively bind multivalent cations (e.g. $Ca^{2+}$, $Ba^{2+}$, $Zn^{2+}$, and $Al^{3+}$) in a gentle and almost temperature independent manner. This gentle solution to gel transition in the presence of selected cations makes alginates an ideal immobilization matrix.

One conventional encapsulation method of forming cross-linked alginate beads involves dissolving or dispersing the bioactive compound, cells or chemical in an alginate solution and promoting cross-linking by dispersing it into a solution containing the cross-linking agent, known as the diffusion setting or external gelation method. However, direct mixing of alginate and multivalent cations rarely produces homogeneous gels due to the very rapid binding kinetics of such ions. The result is a gel or beads with the highest cross-linked alginate concentrations at the outer surface with a decreasing gradient of cross-linking towards the center of the gel. A different approach known as internal gelation mixes alginates with a cross-linking agent (generally $Ca^{2+}$) in a complexed or unavailable form and the cation becomes available as the pH changes. This method is generally accompanied by emulsion and vigorously stirring, or by introducing the cross-linking agent using a crystal gun. In any case, both encapsulation methods are costly, not easily scaled-up and generally limit the particle size to ≥300 μm. Overall, current methods for producing stable alginate gels that involve dropping alginate suspensions into divalent cation solutions are difficult to scale-up and produce undesirably large alginate beads.

In contrast, spray drying is a relatively inexpensive and easily scaled-up technique that is reproducible and one of the most commonly used encapsulation methods in industrial settings. The traditional spray encapsulation process involves dissolving or dispersing the active agent in a sodium alginate solution, forcing the solution through an orifice to form a droplet which is then cross-linked by contact with a calcium chloride solution. Effective spray-drying relies on pumping a low-viscosity solution through an atomizer which has historically precluded ion-mediated cross-linking.

State of art methods for encapsulating biological molecules, cells and chemicals in cross-linked alginates include variations on methods to extrude droplets of alginate/target specie solution into a calcium solution and are limited in the size of the produced particles such that only large (millimeter range) diameters can be achieved. The formation of small (micron-scale), stable particles by spray drying has not been practical due to rapid gelation of alginate upon contact with divalent cations. This process has been limited to producing particles larger than 500 μm.

Microcapsules can contain many different types of materials and can be used for both therapeutic and non-therapeutic applications. In therapeutic applications, the size of the microcapsules can be an important factor in the delivery of the capsules across cell membranes as well as the response made by the cell to the microcapsules. It has been shown that smaller microcapsules approximately 300 μm or less tend to avoid a significant cellular inflammatory or immune response and can efficiently cross membranes compared with larger microcapsules. There are many other uses for microcapsules that are smaller than the 500 µm limits of traditional spray drying methods in a wide variety of applications.

Accordingly, there is a need for methods for efficiently producing small microcapsules with reproducible characteristics that is inexpensive and can be scaled up for industrial applications. The present invention satisfies these needs as well as others and is generally an improvement over the art.

SUMMARY OF THE INVENTION

The present invention generally provides methods for the production and use of microcapsules prepared with a single polymerization step via spray drying of a formulation of a cargo for encapsulation, at least one acid, at least one volatile base, a salt of an acid soluble multivalent ion and at least one type of monomer/polymer. In the preferred method, cross-linking of the polymer is achieved by internal gelation that takes place during spray drying thereby enclosing the cargo in a microcapsule. Ion mediated cross-linking of the polymer molecules is initially prevented by pH control with the volatile base. The timing of the cross-linking is also controlled by the timing of the volatilization of the base, which lowers the pH and releases the ions to spontaneously form cross-links between the polymer molecules.

The methods are particularly useful for spray-drying applications where premature cross-linking of the polymers prevents effective atomization of the product. In the spray-drying application, the pH of a formulation that includes polymer molecules, an acid and a salt of a divalent ion is controlled with a volatile base such that the divalent ions are made available only post-atomization and upon vaporization of the base. Additionally, the release behavior (rates and extent) of the encapsulated moieties in aqueous suspensions can be further controlled by the incorporation of (a) hydrophobic compound(s) in the spray-drying formulation to control the particle hydration properties.

The methods are illustrated with the spray-drying of an aqueous formulation that contains sodium alginate, a calcium salt that is only soluble at reduced pH and an organic acid that has been neutralized to a pH just above the pKa with a volatile base. Under these conditions, the calcium salt is insoluble and calcium ions are not available for cross-linking. The solution in this fluid state is pumped through the nozzle of the spray dryer, where it is effectively atomized. Upon atomization, the volatile base is vaporized, which reduces the pH (hydrogen ions are released into solution) and in turn releases calcium ions from the calcium salt that are now available to cross-link the alginate. The incorporation of an additional hydrophobic polymer to the formulation allows for the control of hydration properties of the particles to control the release of the encapsulated compounds.

This same process can be used for encapsulation using soy or whey proteins, polygalacturonates (pectins) and other polymers that will spontaneously cross-link in the presence of multivalent cations. The formulation can also be a mixture of matrix polymer types including mixtures of polymers and proteins and copolymers. Formulations with mixed polymer types can improve protection of the biological compound that is being encapsulated.

The terms “monomer” and “polymer” are used interchangeably herein in the general sense to refer to the molecular entity or unit that has at least one polymerizable moiety that cross-links in the presence of a multivalent ion and the terms are not intended to be limiting. The polymerized unit may be a singular monomer or may be oligomeric. Any molecule that polymerizes with multivalent ions is a candidate monomer/polymer.

Preferred volatile bases include ammonium hydroxide and volatile amine compounds such as methylamine. While these volatile bases are preferred, it will be understood that many different types of volatile bases could be selected.

The modulation of the pH of the formulation is by the acid or combination of acids that are selected. The preferred acid is an organic acid. An anti-oxidative acid can also be used instead of, or as a supplement to, the organic acid in the formulation to increase protection for oxygen-sensitive biocompounds in one embodiment.

The preferred salts of multivalent ions that initiate polymerization are divalent ions such as $Ca^{2+}$, $Ba^{2+}$, and $Zn^{2+}$. Dicalcium phosphate is particularly preferred. See Table 1.

The formulation can also include other functional compounds such as hydrophobic compounds that can influence release rates of the cargo from the microcapsule. The formulation can also include surface-active compounds to influence particle size and size distributions.

Although the methods are generally directed at employing conventional spray-drying to encapsulate active agents in matrix particles, other encapsulating systems can also be used to produce core-shell microcapsules. For example, various bi-fluid annular nozzles can be used. Likewise, other coating processes such as spinning disc systems can be used.

The present methods have been shown to produce stable cross-linked alginate particles in a single step by spray drying. This approach yields small (median particle sizes in the range of 15-120 μm), insoluble particles whose production could be easily scaled-up for industrial applications. The operational parameters can also be controlled to affect product properties such as particle-size and particle-size distribution.

Furthermore, the activity of the encapsulated bioactives was not compromised by the methods. Cellulolytic enzymes (cellulases and xylanases) were encapsulated and tested on their different substrates to verify retention of activity. There was no difference in enzyme activity between the encapsulated enzymes and equivalent enzyme loadings that did not undergo spray drying. This demonstrated that enzymes encapsulated by this spray-drying method can retain full activity. The controlled release of encapsulated ingredients was also demonstrated.

According to one aspect of the invention, a one-step process is provided that includes almost simultaneous particle formation, particle cross-linking and particle drying.

Another aspect of the invention is to provide a method for a) controlling the timing of calcium-mediated cross-linking of polymers such as alginates and soy or whey proteins to enable spray-dry encapsulation of biological moieties, b) controlling the release of the encapsulated ingredients by controlling cross-linking and hydration properties of the encapsulation, and c) increasing yields of cross-linked alginate (or soy or whey protein) particles and controlling particle size and narrowing size distribution.

Yet another aspect of the invention is to provide a microencapsulation method that can be adapted for use with many different types of biocompatible polymers such as alginate, soy protein, whey protein, chitosan, and pectins.

A further aspect of the invention is to provide a method that can be modulated to control the microcapsule structural characteristics and produce capsules of consistent sizes that is easy to use and inexpensive to produce.

Another aspect of the invention is to provide a method that can be used in multiple industries employing spray-drying to encapsulate active agents such as encapsulating biological molecules, cells, probiotics, nutraceuticals and other organic or inorganic chemicals.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
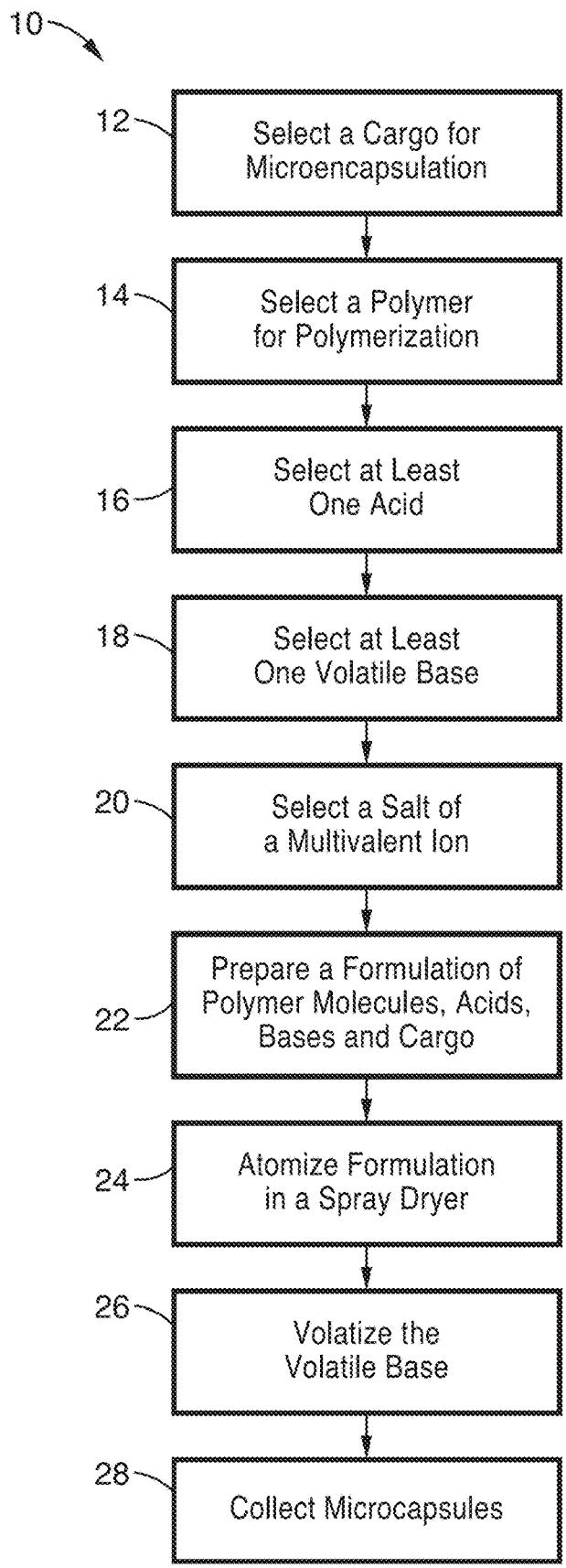
FIG. 1 is a flow diagram of a method for producing microcapsules using a single spray-drying step according to one embodiment of the invention.

Referring more specifically to the drawings, for illustrative purposes several embodiments of the materials and methods for producing a range of small microcapsules containing selected cargo in a one step spray drying method of the present invention are depicted generally in FIG. 1 through FIG. 8. It will be appreciated that the methods may vary as to the specific steps and sequence and the microcapsule architecture may vary as to composition and structural details, without departing from the basic concepts as disclosed herein. The method steps are merely exemplary of the order that these steps may occur. The steps may occur in any order that is desired, such that it still performs the goals of the claimed invention.

Methods for microencapsulation of cargo in a stable, cross-linked polymer matrix are provided utilizing spray-drying polymerization in a single polymerization step. The methods consistently produce small capsule sizes and the characteristics of the capsule can be controlled. Cargo, that is selected by the user and contained in the core or matrix of the microcapsule, may be exposed to the exterior in some embodiments because the shell is permeable to allow the controlled release of the encapsulated cargo. The permeability of capsule also allows the interaction of the encapsulated cargo with the surrounding environment.

An alginate encapsulation of a protein cargo is used to illustrate the method. In this method, an aqueous formulation that contains sodium alginate, a calcium salt that is only soluble at reduced pH and an organic acid that has been neutralized to a pH just above the pKa with a volatile base. Calcium ions needed for cross-linking become available during spray drying by volatilization of the volatile base and the consequent drop in the pH of the spraying solution permitting cross-linking of the alginate polymer.

By way of example, and not of limitation, FIG. 1 illustrates schematically a method 10 for producing microcapsules from a formulation that is aerosolized into droplets through the use of an annular nozzle, spinning disc technology or some other fine droplet forming device such as spray-drying.

At block 12 a cargo is selected for encapsulation within the size controlled microcapsules. A wide variety of cargo can be selected and encapsulated for different uses. For example, the cargo can be organic or inorganic molecule compounds such as proteins, nucleotides, drugs, medicinal compositions, anti-bacterial agents or probiotics for animal or human treatments. The cargo can also be individual cells, such as stem cells, for implantation. The cargo can also be selected for non-therapeutic uses such as aromatic compounds, oils, catalysts, initiators and other industrially relevant compounds.

A monomer, polymer or other unit that can be cross-linked in the presence of multivalent ions is selected at block 14. The selection of the cargo and the ultimate use of the microcapsules will influence the selection of the polymer or mixture of polymers/monomers that are used at block 14. For example, if the ultimate use of the microcapsules is intended to be as an implant in the human body, the selection of the polymer/monomer at block 14 would be one that is biocompatible as well as one that does not trigger a significant immune or inflammation response. If the ultimate use of the microcapsules is intended as part of a tablet to be ingested, then a polymer can be selected at block 14 that will produce a microcapsule that is resistant to degradation in low pH environments and changing environments.

Cross-linked alginates have been shown to remain mostly intact in gastric environments (i.e. in the stomach) while dissolving in the intestines. Thus compounds that are encapsulated by cross-linked alginates remain protected in the acid environment of the stomach and only released once in the intestines. This is advantageous because 1) absorption (of nutrients etc) largely occurs in the large intestines, and 2) this can protect compounds that are otherwise acid labile.

Monomers that are selected at block 14 need to cross-link in the presence of multivalent ions but not necessarily at low pH conditions. In the embodiment of the invention shown in FIG. 1, the lower pH conditions makes the multivalent ions available for cross-linking that are unavailable at a higher pH. The invention is not necessarily limited to low pH conditions, only the availability of multivalent ions.

Suitable polymers can include organic polymers and proteins such as alginate, chitosan, collagen, latex, polygalacturonates (pectins), soy and whey proteins. The capsule polymer matrix can also be formed from a mixture of such polymers (e.g. alginates and proteins). The polymers selected at block 14 can also be a combination of polymers and co-polymers such as acrylic latex. Formulations with mixed polymer types can improve protection of the encapsulated biological compound.

Once the polymer is selected at block 14, at least one acid is selected at block 16, at least one volatile base is selected at block 18, and the salt of a multivalent ion is selected at block 20. The salt of the multivalent ion that is selected at block 20 is preferably only soluble at a reduced pH and the selected organic acid or acids will be neutralized to a pH just above the pKa with the selected volatile base. Additionally, Table 1 and Table 2 provide partial lists of calcium salts and acids, respectively, which can be selected at blocks 16 and 20. Although calcium salts are illustrated, it will be understood that other salts of multivalent ions can also be selected.

Of the multivalent ions that are capable of cross-linking monomers, divalent ions and trivalent ions are particularly preferred. Any salt of a divalent or trivalent ion that is soluble only under acidic conditions can be selected at block 20 and used. For example, salts of barium ($Ba^{2+}$), beryllium ($Be^{2+}$), calcium ($Ca^{2+}$), chromium ($Cr^{2+}$), cobalt ($Co^{2+}$), copper ($Cu^{2+}$), iron ($Fe^{2+}$), lead ($Pb^{2+}$), magnesium ($Mg^{2+}$), mercury ($Hg^{2+}$), strontium ($Sr^{2+}$), tin ($Sn^{2+}$), and zinc ($Zn^{2+}$) can be used. However, dicalcium phosphate, calcium carbonate, calcium oxalate are particularly preferred.

The acid that is selected at block 16 is preferably matched with the volatile base selected at block 18 so that cross-linking will occur with the monomers with the volatilization of the base. In one embodiment, an anti-oxidative acid is used instead of or in combination with the organic acid in the formulation to increase protection for oxygen-sensitive biocompounds. The capsule in this setting has the potential for exhibiting the anti-oxidative properties of the formulation.

Suitable acids that are selected at block 16 include carboxylic acids such as succinic acid and adipic acid, and phenolic acids such as, ascorbic acid, gallic acid and caffeic acid. The acid in the formulation is preferably an acid with a pK in the 4 to 5.5 range.

The volatile base that is selected at block 18 includes ammonia hydroxide, and other volatile amines such as hydrazine, methylamine, trimethylamine, ethylamine, diethylamine, triethylamine, isobutylamine, N,N-diisopropylethylamine, morpholine, piperazine, and ethylenediamine.

At block 22, the selected acids, bases, salts and cargo are mixed together to produce a formulation to be atomized and spray dried. The quantities of each component of the composition are determined by the pH of the resulting formulation and can be optimized. The formulation must have a pH that maintains the selected multivalent salt as an insoluble salt until liberation by the volatilization of the base. In one other embodiment, the components of the final formulation are divided and mixed at the nozzle head at the time of atomization at block 24.

The formulation is preferably atomized in a spray dryer or spinning disc dryer or other device that will produce droplets of a desired diameter at block 24. The operational parameters of the apparatus can be controlled to affect capsule properties such as particle-size and particle-size distribution. The spray dryer preferably produces capsules in the range of between approximately 15 μm and approximately 400 μm in diameter and capsule diameters ranging from approximately 15 μm to approximately 120 μm are particularly preferred.

The droplets that are formed in the spray drying apparatus are heated to further volatilize the volatile base in the formulation at block 26 to initiate the polymerization of the polymers and the formation of the capsules. The volatilization of the base changes the pH of the formulation allowing the salt to disassociate so that multivalent ions are available for cross-linking of the monomers.

In another embodiment, an annular nozzle is used at block 24 that has a cross-section consisting of two concentric circles where the core containing the biocompound or chemical cargo flows in the inner circle while the shell formulation flows from the outer ring. The resulting droplet from the nozzle will have the biological compound or chemical cargo in the core of the droplet, while the encapsulating polymer fully surrounds the core, forming a shell. The droplets are preferably formed in the drying chamber of the apparatus where the volatile base is driven off at block 26, releasing the divalent cations and cross-linking the negatively charged polymers of the shell.

For high melting solid particles, in another embodiment, the encapsulation process takes place utilizing spinning disc technology. The solid particles of the cargo are first dispersed in the alginate solution containing all the other required ingredients and then dropped onto the spinning disc where the alginate solution coats particles undergoing centrifugal motion. The coating is then solidified by dropping the coated particles through a heated fluidized bed where the ammonia and water are flashed off.

One particularly preferred illustration of the method is with a formulation composed of alginates, adipic acid (pKa=4.43 and 5.41 at 25° C.) or succinic acid (pKa=4.16 and 5.61 at 25° C.) and a calcium salt of low solubility in water, where the pH is controlled by the addition of ammonium hydroxide. Alginates are mixed polysaccharides of $\beta 1\rightarrow 4$ mannuronic acid and $\beta 1\rightarrow 4$ guluronic acids. In a solution with a pH>4, the polysaccharide backbone is negatively charged, with pKa's of 4 and 3.2 for the mannuronic acid and guluronic acid residues, respectively. The ammonium hydroxide base is titrated to adjust the pH of the solution to above the second pKa of the acid, thus minimizing the hydrogen ion concentration in the solution and maintaining the calcium as an insoluble salt (i.e. not available for cross-linking). The solution in this fluid state is preferably pumped through the nozzle of the spray dryer, where it is effectively atomized. Upon atomization, the volatile ammonia is vaporized which reduces the pH (hydrogen ions are released into solution) and in turn releases $Ca^{2+}$ ions that electrostatically cross-link the negatively charged backbones of the alginates.

For example, in one embodiment an alginic acid (alginate) solution (4%) can be used that contains alginic acid, unavailable calcium ions in the form of dicalcium phosphate, and citrate, a chelating agent to complex low concentrations of calcium ions. Biomolecules or other molecules to be encapsulated are added to the alginic acid solution.

An adipic acid or succinic acid solution (4%) is neutralized to a pH that is adjusted to above its second pKa (5.4 or 5.6, respectively) using ammonium hydroxide. The alginic acid solution and the neutralized acid solution are mixed to a ratio of 1:1. No cross-linking will occur with the mixing. The mixed solution is then spray dried. During spray drying, the ammonia is volatilized which lowers the pH of the solution and releases the calcium ions and cross-links the alginates during atomization. The biomolecules (or other added molecules) are entrapped within the alginate matrix.

Optionally, hydrophobic compounds such as latex or waxes can be added to the formulation before spray drying. In an alternative embodiment, release characteristics of the encapsulated moieties in aqueous suspensions can be controlled by the incorporation of hydrophobic compounds in the spray drying formulation. The presence of hydrophobic compounds in the formulation producing the spray dried product modulates the hydration properties of the capsules, thus controlling the rate of water intrusion into the capsules and the diffusion of encapsulates out of the particles. Examples of optional hydrophobic compounds in the formulation include (but are not limited to) polymer latexes and wax emulsions.

Finally, the microcapsules are collected at block 28 and may be subject to further processing such as further curing or may receive additional coatings depending on the ultimate use of the microcapsules. The microcapsules may also may be separated according to size.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the methods, alginates were used as the matrix for encapsulating a mixture of plant cell wall degrading enzymes. Spray-dried sample and controls that are described in this example are provided in Table 3.

The microcapsule samples set forth in Table 3 were prepared from the following formulations: Control A consisted of 50 mL of a 2% solution of Manugel® L98 (FMC) in purified water and Control B consisted of 50 mL of a 1:1 mixture of 4% Manugel® L98 in water and a 4% adipic acid solution with pH taken to 5.5 by the addition of a volume of 29% ammonium hydroxide solution. The sample identified as Example 1 in Table 3 was made from 50 mL of a same mixture as Control B with the addition of 48 mg of an enzyme mixture consisting of Celluclast®, Novo 188® and NS50030 (Novozymes) in a 2:1:1 ratio. Control C consisted of 50 mL of a 1:1 mixture of 4% Manugel® L98 in water with a 4% adipic acid solution. All solutions were mixed before atomization. Spray drier Model B-290 (BUCHI) was used in the experiments. All atomizations were performed at maximum air flow, 10% pump intensity, 78% aspirator intensity and 150° C. inlet temperature. In all cases, all the volume was pumped into the nozzle and the recovered spray-dried product was weighed to estimate mass recovery.

Effective cross-linking of the alginates during spray drying was evidenced by (1) minimal dissolution of the cross-linked alginate particles in water and (2) the larger average sizes of the cross-linked alginate particles than the noncross-linked alginate particles. The extent of the dissolution of each of the alginates was assessed by measuring the viscosities of the supernatants of aqueous suspensions of the spray-dried particles.

Figure 2:
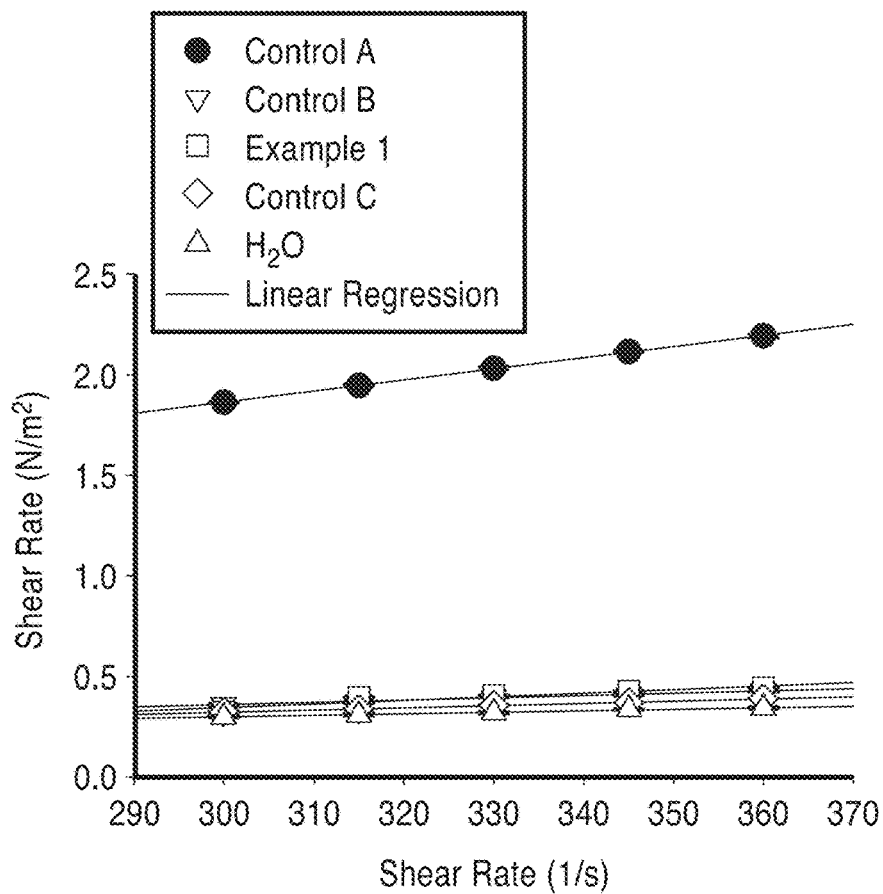
FIG. 2 is a graph plotting shear stress versus shear rate measurements of the supernatant of spray-dried particle suspensions stirred vigorously in water overnight.

The resistance of cross-linked alginates to dissolution was verified by measuring the viscosities of the supernatant in aqueous suspensions of the spray-dried particles. The non-cross-linked (Control A) and the cross-linked particles (Control B, Control C and Example 1) (50 mg) were added to 5 mL of water and stirred vigorously overnight. The alginate suspensions were centrifuged for 4 minutes at 3452×g and the supernatants were collected. The viscosity of the supernatants was measured in a Brookfield DV-II+Pro cone and plate viscometer (Brookfield Engineering). Alginate suspensions stirred for one-hour and 4-days gave similar results. The shear stress versus shear rate measurements of the supernatant of spray-dried suspensions are shown in FIG. 2 and in Table 4.

Figure 3:
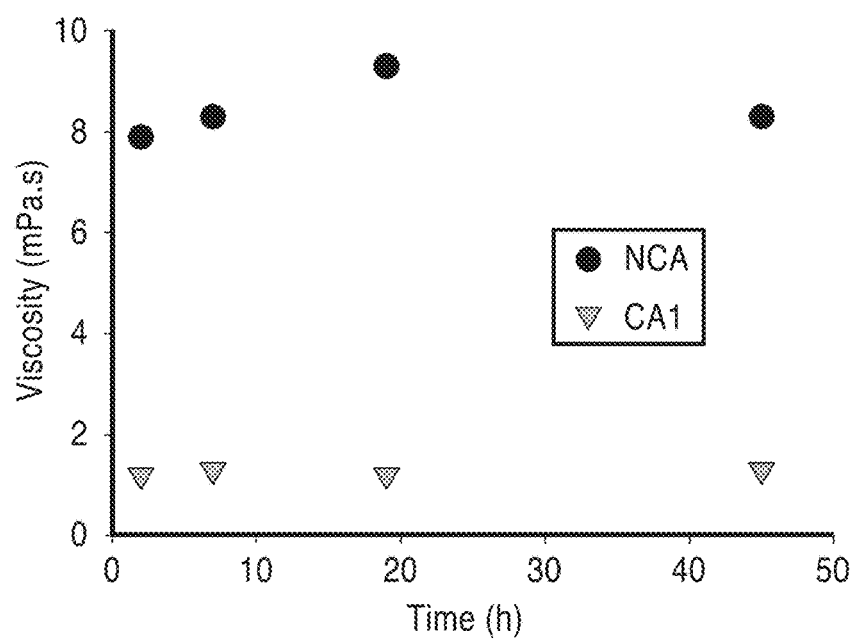
FIG. 3 is a graph plotting viscosity in the supernatant of spray-dried alginate suspensions over time.

The viscosity in the supernatant of spray-dried alginate suspensions over time is shown in FIG. 3. The same alginate-based mass of non-cross-linked (NCA) and cross-linked (CA1) alginate particles were suspended in water (2.5% w/v) and the viscosity of the supernatant was recorded over time. Viscosities were obtained from the slopes of shear stress vs. shear rate curves.

The stability of the cross-linking of the alginates in the spray-dried particles was evaluated by measuring the viscosities of the supernatant of suspended particles over the course of 45 hours. FIG. 3 shows that the non cross-linked alginate particles (NCA) dissolved rapidly in water, resulting in a highly viscous solution (8 mPa·s) within 2 hours. In contrast, the cross-linked alginate particles (CA1) did not dissolve and their supernatant viscosity remained close to unity throughout the 45-hour incubation in the aqueous suspension (FIG. 3). Highly stable alginate particles are advantageous in several biomedical applications such as cell immobilization (i.e. stem cells or probiotics) where cell entrapment is crucial for increasing their survival, facilitating their delivery and conferring protection from immune responses.

In other samples, the spray-dried particles from a formulation containing alginates but no calcium (NCA) and a formulation not designed to avail calcium during atomization (NCM) gave supernatant viscosities of 9.3 mPa·s and 3.8 mPa·s, respectively. These viscosities, significantly higher than that of water (0.9 mPa·s), indicated that the spray-dried particles readily dissolved in water. Conversely, the viscosities of the supernatants of spray-dried particles that were formulated to promote alginate cross-linking during spray drying were only slightly higher than that of water (1.2-1.3 mPa·s), indicating minimal dissolution of these particles in water.

Increasing the alginate: $Ca^{2+}$ mass ratio in the formulation resulted in higher supernatant viscosity (3.3 mPa·s) suggesting insufficient cross-linking in that sample. The amount of cross-linking agent, besides other factors such as molecular weight of the alginates, the G/M ratio and the block structure of the alginate source, will affect the extent of cross-linking. In another sample, no effort was made to prevent gelling prior to spraying, which resulted in a significantly decreased yield of 20% (mass recovery) as compared to up to 67% from all other formulations due to difficulties in pumping and atomization.

Overall, the data given in Table 4, FIG. 2 and FIG. 3 demonstrate that significant dissolution of the alginates occurred in the suspension of the non-cross-linked alginate particles (Control A) as evidenced by a significant increase in the viscosity of the supernatant. In contrast, the supernatant of the suspensions containing cross-linked particles (Control B, Control C and Example 1) maintained low viscosities, thus indicating limited dissolution of the matrix.

Example 2

Particle size distributions of the spray-dried particles were analyzed by Mie scattering in the Mastersizer 2000 Particle Size Analyzer (Malvern). The capsule particles were dispersed in ATLOX 4912 (a polymeric surfactant) in corn oil. Capsule sizing was conducted in an organic phase to minimize the effects of particle swelling that would occur in an aqueous phase, thus more accurately representing the actual size of the spray-dried particles. The size distribution data for non-cross-linked alginates and cross-linked alginates (with and without encapsulated enzymes) are shown in FIG. 4.

Figure 4:
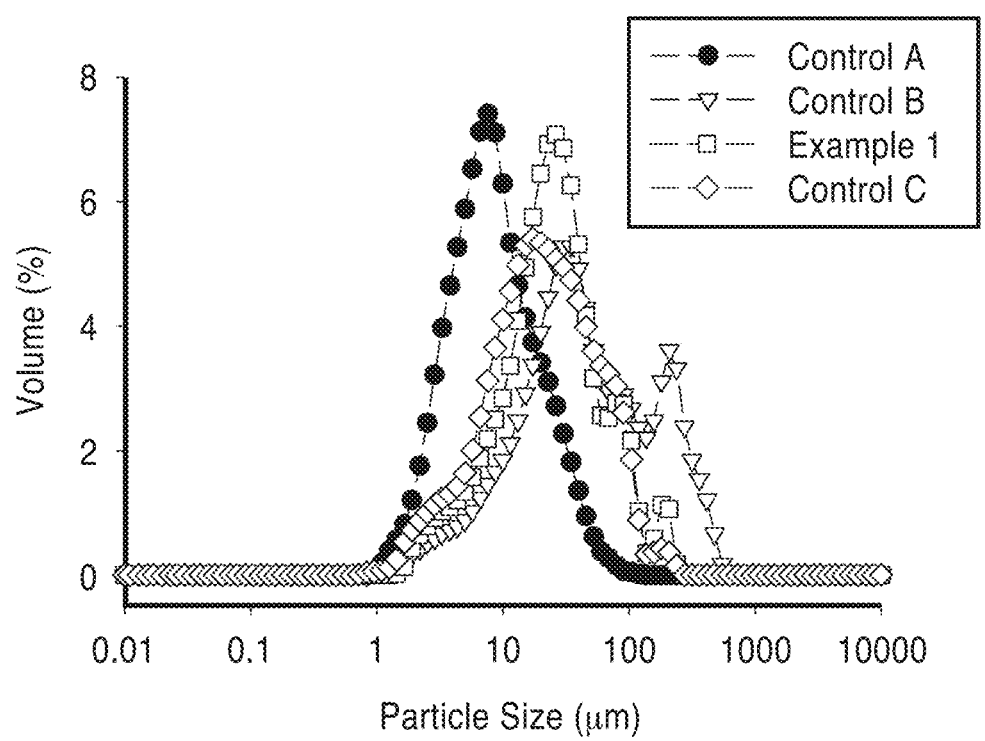
FIG. 4 is a graph plotting size distribution of spray-dried particles as measured by Mie Scattering in oil.

It is interesting to note in FIG. 4 and Table 5, that the median particle sizes are generally larger (by approximately 5 to 10 times) for the cross-linked particles than for the non-cross linked particles. This observation was consistent regardless of the timing of the cross-linking (before or after atomization). The median particle size for enzyme-encapsulated particles was 23 μm. Cross-linked particles appear to be more polydisperse, with a bimodal particle size profile.

A shift towards larger particle sizes was observed in all of the tested cross-linked alginate samples as compared to the non-cross-linked samples in addition to those illustrated in FIG. 4. The median size of non-cross-linked alginate particles was approximately 5 μm with most capsule particles within 2.3 µm and 10.4 µm diameter sizes. In contrast, tested cross-linked alginate particles were more polydisperse, with median diameters ranging from 15 to 120 µm depending on the sample formulation.

This variation in particle size is likely the result of differences in solute concentrations, solution viscosity, rates of volatilization of ammonia and rates of cross-linking during spraying that impact droplet formation and drying kinetics. Solutes alter surface tension and vapor pressure of a solution to impact droplet formation in the spray and thus particle size in the dried product, with smaller particles obtained at lower solute concentrations. Solute concentrations will also impact the solution viscosity, thus affecting the size of the droplets formed during atomization. A surfactant in the solution would lower surface tension and improve drying kinetics to control for small particle sizes. Solute concentrations in the cross-linked alginate samples were higher than in the non cross-linked samples due to the addition of the organic acid and ammonium hydroxide.

Example 3

To evaluate enzyme release from the encapsulation matrix over time, microcapsules were produced with a cargo of a cellulase-xylanase mixture in an alginate capsule. Sodium alginate samples were prepared by completely dissolving sodium alginate (4% or 2% w/v) in an aqueous solution containing citric acid (0.06%) and dicalcium phosphate (0.2%) and (in some cases) latex at various concentrations, and then mixing 1:1 by volume with succinic acid (4% w/v, pH 5.6 adjusted using ammonium hydroxide).

The enzyme cargo was a mixture of Celluclast®, Novo 188® and NS 50030 (Novozymes A/S) that was mixed in a 2:1:1.8 ratio by volume. One volume of the enzyme mixture was diluted by mixing with three volumes of sodium acetate 5 mM (pH 5) containing 0.02% sodium azide as preservative and concentrated in an stirred cell (Amicon) with a 10 kDa MWCO membrane (Millipore).

Figure 5:
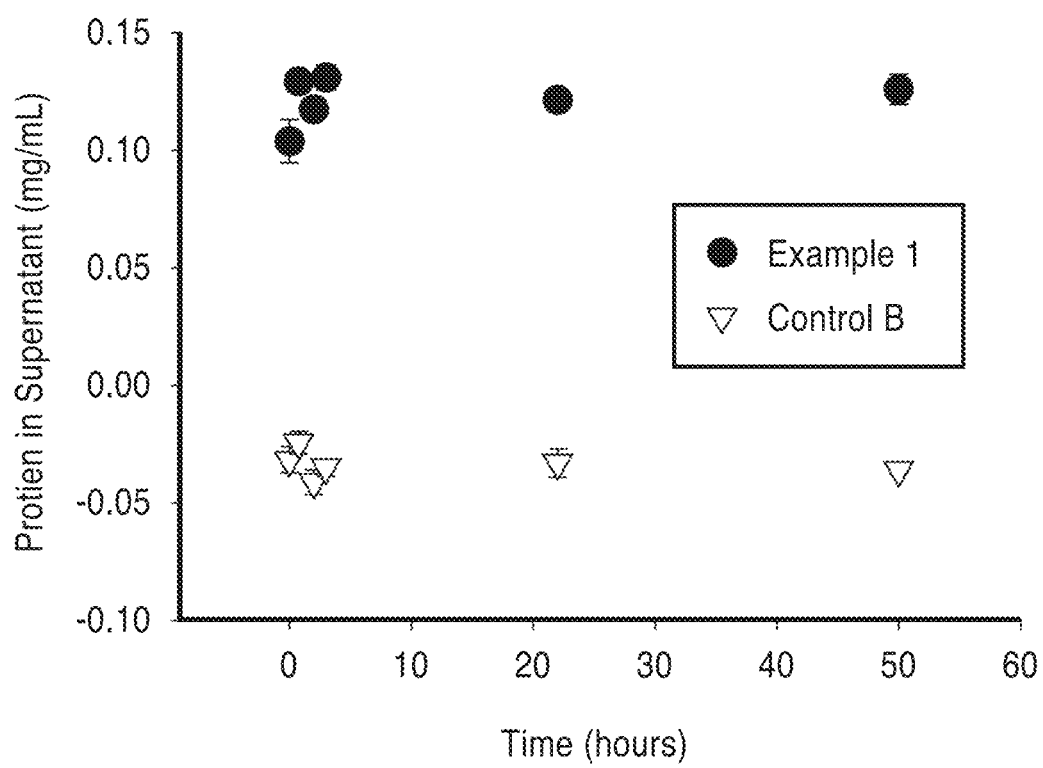
FIG. 5 is a graph showing enzyme (protein) concentration in the supernatant of suspensions of encapsulated enzyme particles.

Enzyme diffusion tests were performed where encapsulated enzymes were suspended under continuous agitation in an aqueous buffer (5 mM sodium acetate, pH 5) and sampled over time and the results shown in FIG. 5. The concentration of protein in the final enzyme mixture was measured by the Bradford assay (Biorad), where increasing protein concentration in the supernatant indicated an increased diffusion of enzyme into the bulk solution from the encapsulated particles. The data in FIG. 5 demonstrates that mass transfer is rapid and the bulk of the diffusion occurs within the first 5-hours. The diffusion of enzymes out of the encapsulated particles, therefore, is not limited.

Figure 6:
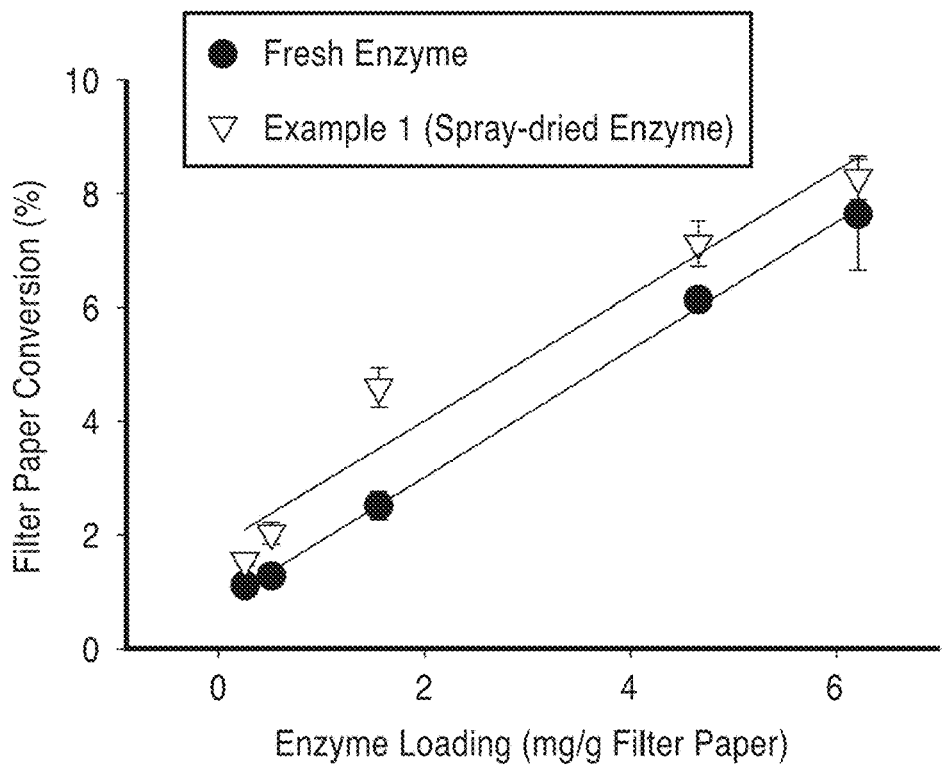
FIG. 6 is a graph of filter paper activity (FPA) of enzymes from liquid and spray-dried sources.
Figure 7:
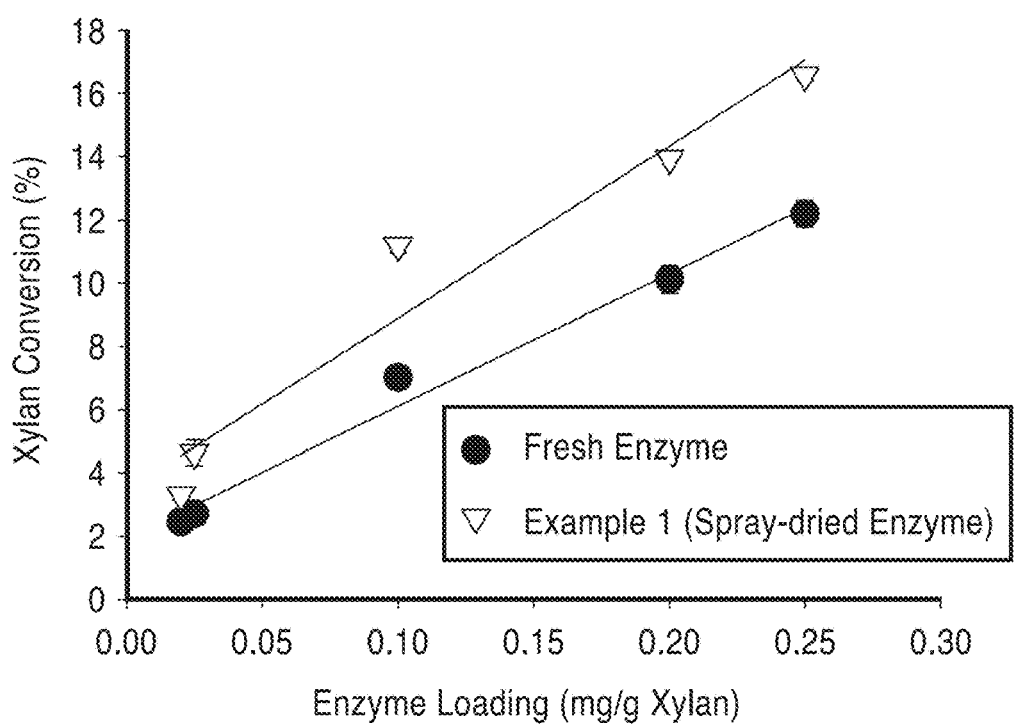
FIG. 7 is a graph showing xylanase activity in liquid and spray dried enzymes.

The activity of the encapsulated enzymes was also evaluated. The activity of the enzyme mixture in the liquid and spray-dried forms was then compared and no loss in cellulase and xylanase activity was observed as shown in FIG. 6 and FIG. 7.

Cellulase activity was measured on Whatman No. 1 filter paper by incubating the original enzyme mixture and the supernatant of a suspension of spray-dried particles for 1 hour at 50° C. in 5 mM sodium acetate buffer.

Xylanase activity was similarly measured using birchwood xylan as substrate instead of filter paper and incubating for 15 minutes. Enzymatic reactions were carried out using freshly spray-dried particles as well as particles that had been stored for up to 1 month, to verify there was no loss of activity upon storage.

Activities of the spray-dry encapsulated enzymes were tested against activities of the free enzymes in solution on the basis of equivalent protein loadings. Reactions were carried out in 5 mM sodium acetate pH 5 with 0.02% sodium azide in 400 mL total volume at 50° C. Incubation times were 60 minutes and 15 minutes for filter paper activity (FPA) and xylanase activity, respectively. Cellulase and xylanase activities were estimated by measuring the amount of reducing sugars produced in each reaction. Released sugars were quantified by the dinitrosalicylic (DNS) assay using glucose and xylose standard curves, respectively. Control reactions using spray-dried powder (with no encapsulated enzyme) plus equivalent concentrations of free enzymes in solution were conducted to verify that other factors in the supernatant of spray-dried particles (i.e. dissolved solids or free alginates) were not interfering with the reaction. It was observed that all the enzyme mixtures tested contained the same ratios of Celluclast, Novozyme188 and the NS50030 on a volume basis.

Example 4

To further demonstrate the encapsulation methods, alginates were used as a matrix for encapsulating bovine serum albumin (BSA) with the inclusion of latex molecules in the spray-drying formulation to retard the release of encapsulated BSA in aqueous suspensions. Spray-dried samples described in this example are given in Table 6. Samples were prepared as follows: CA1±BSA consisted of a 1:1 mixture of 2% solution of sodium alginate (Sigma-Aldrich cat. no A2158) sodium citrate (0.06%) and dicalcium phosphate (0.2%) in water and a 4% succinic acid solution with pH taken to 5.6 by addition of a 29% ammonium hydroxide solution. CA1L0.05±BSA consists of a 1:1 mixture of 1% solution of sodium alginate, citric acid (0.06%) and dicalcium phosphate (0.2%) and latex (0.05%) in water and a 4% succinic acid solution with pH taken to 5.6 by addition of a 29% ammonium hydroxide solution. The same formulation is prepared for CA1L0.25±BSA and CA1L0.5±BSA with the exception of 0.25% and 0.5% latex loading, respectively, instead of 0.05% latex loading. For all samples, the '±BSA' indicates that samples with and without BSA were prepared, where 0.15% (w/v) of BSA was added to the +BSA formulation shortly before spray drying. All solutions were mixed before atomization. Spray drier Model B-290 (BUCHI) was used in the experiments. All atomizations were performed at maximum air flow, 20% pump intensity, 100% aspirator intensity and 150° C. inlet temperature. The latex used was chosen for its glass transition temperature of 75° C., which is lower than the outlet temperatures of approximately 80° C. In all cases, all the volume was pumped through the nozzle.

During spray-drying, volatilization of the ammonia from the atomized droplet reduces the solution pH to approximately 4.2 to 4.4 (the first pKa of the organic acid present in the formulation). In this pH range, BSA has a net-positive charge (pI=4.7), thus facilitating strong attractive electrostatic interactions with the negatively charged carboxyl groups of the alginates.

The cargo was a standard BSA solution (0.15% w/v in $H_2O$; Thermo Scientific) that was added to the spray-drying solution right before spray drying. Moisture content of the spray-dried samples was measured in a Mettler Toledo HR83 halogen moisture analyzer, following manufacturer guidelines and using three replicates per sample. The spray-dried samples were stored in a desiccator with anhydrous calcium sulphate (Hammond Drierite Company, Xenia, Ohio).

Time-course protein diffusion from cross-linked alginate particles into the liquid phase was obtained by taking 250 mg of the spray-dried powder and adding 5 mL 0.02% NaN$_3$ (aqueous solution) and mixing thoroughly. Samples were centrifuged (1 min at 562×g) at different time points and 100 mL aliquots of the supernatant were collected. Protein in the supernatant was quantified using the Pierce BCA protein assay using BSA standards.

Spray-dried samples without protein but otherwise with identical formulations were used as a control. The extent of protein diffusion out of the spray-dried particles was determined as the total mass of the protein measured in the supernatant as a percent of the total protein added. No interference of non-cross-linked alginates and/or latex in the supernatant with the protein quantitation assay was noted, verified by measuring a known amount of BSA added to control samples.

Example 5

The release of encapsulated BSA in aqueous suspensions was evaluated to demonstrate the permeability of the microcapsules. BSA release from cross-linked alginate particles into the liquid phase was obtained by mixing 250 mg of the spray-dried powder and 5 mL 0.02% NaN$_3$ (aqueous solution). Samples were centrifuged (1 min at 562×g) at several time points and 100 µL aliquots of the supernatant were collected. Protein in the supernatant was quantified using the Pierce BCA protein assay that is based on the 2,2'-bicinchoninate method using BSA standards. Spray-dried samples without protein but with otherwise identical formulations were used as a control.

In this illustration, varying amounts of hydrophobic styrene acrylic latex was added to the formulations to affect protein release from the spray-dried particles. The latex that was used was chosen based on its glass transition temperature (Tg) of 75° C., slightly below the outlet temperature during spray drying (80° C.) to promote softening during spraying and fusing during drying in the particles.

The extent of protein diffusion out of the spray-dried particles was determined as the total mass of the protein measured in the supernatant as a percent of the total protein added. No interference of non cross-linked alginates and/or latex in the supernatant with the protein quantitation assay was observed, verified by measuring a known amount of BSA added to control samples. Results shown in FIG. 8 demonstrate that increasing levels of latex in the spray-dry formulation decreased BSA release rates and the extent of release (with the 70 hours that were tested).

Figure 8:
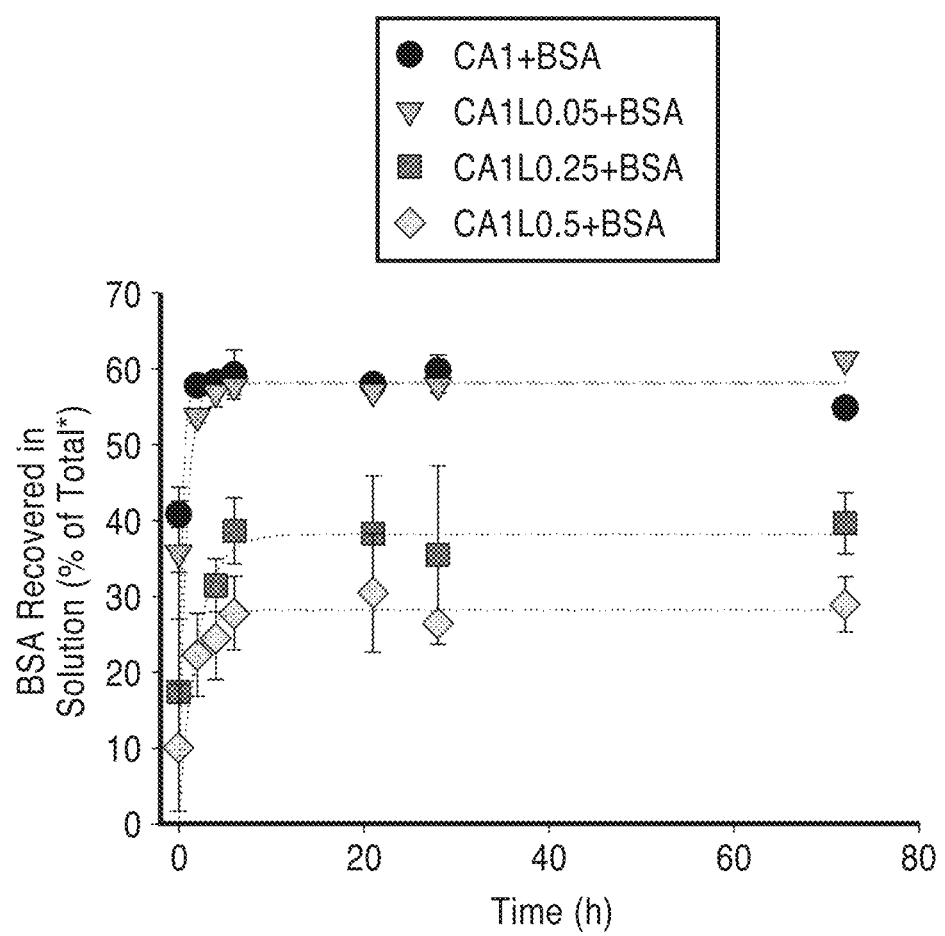
FIG. 8 is a graph plotting BSA protein release from cross-linked alginate encapsulation in aqueous suspensions.

Release characteristics of the encapsulated BSA were examined by measuring the rate of protein diffusion out of the particles into aqueous media. Only up to approximately 65% of the added protein was measured in the liquid phase for any of the samples tested as seen in FIG. 8. Furthermore, incubation for an extended 3-day period with 1% (v/v) Triton X-100 and brief sonication did not increase the amount of protein released from the particles. In addition to measuring total nitrogen in the spray dried samples, several different commercially available protein assays (Bradford Protein Assay (Bio-Rad), BCA Protein Assay (Pierce) and Quant-iT Protein Assay (Invitrogen)), were used to attempt to measure the amount of protein encapsulated in the spray-dried particles.

A relatively fast initial release rate of the encapsulated BSA was observed as seen in FIG. 8 that may be due to large pores in the cross-linked alginate beads or to BSA being at the surface of the particles. BSA is a surface-active protein that will preferentially partition to the air/water interface during droplet formation, and it has been observed that BSA adsorption at the air/water interface is a rapid process. Addition of low-molecular weight surfactants that would out-compete larger molecules such as proteins for the air/water interface would prevent the rapid release of the encapsulated compound.

There were notable differences in release rates between the different formulations in the first 6 hours, where higher latex contents appear to correlate with lower rates and extents of release as seen in FIG. 8. The lowest amount of latex added (0.05 g latex/g alginates, CA1L0.05) had minimal impact on BSA release. Increasing latex content in the formulation trended with decreasing total recovery of BSA in the supernatant. A linear fit of the BSA recovered in solution with respect to latex content yields an $R^2$ value of 0.94 (not shown). The hydrophobic latex incorporated into the encapsulation matrix may inhibit water diffusion into the particles, thereby limiting the release of BSA. The addition of water insoluble substances to the alginate matrix was shown to modify the surface porosity and improve entrapment of the encapsulated moieties.

Example 6

Manipulation of the capsule size and capsule permeability were also demonstrated. It was observed that the addition of BSA to the formulations impacted the size and shape of the spray-dried particles. BSA-containing capsules were smaller and had a narrower particle size distribution compared to those capsules without BSA but with an otherwise identical formulation. Additionally, the BSA-loaded particles had more regular and homogeneous shapes. BSA is a globular, surface-active protein that likely decreased surface tension in the spray, thus resulting in smaller droplets with faster drying kinetics. Furthermore, BSA-containing formulations resulted in increased yields on a mass basis with less sample lost in the cyclone, possibly due to the improved drying. In contrast, the formulation containing the cellulase/xylanase mixture yielded larger, more polydisperse particles.

In addition, components other than the enzymes present in the preparation (such as sorbitol) may result in an increase in the viscosity and a decrease in the vapor pressure of the spraying solution resulting in larger droplets, slower drying and lower mass recovery.

Moreover, further optimization of spray-drying conditions could yield even smaller particles. For example, increasing air pressure through the atomizer, or the use of alternate nozzle configurations could improve spray atomization and decrease particles size. Alternatively, the feed rate has a direct influence on the outlet temperature.

Normally it is preferred that the feed rate be minimal to allow for good drying of the particles with an outlet temperature between approximately 72° C. and 80° C. Increasing the feed rate will decrease the outlet temperature and can result in microcapsules that insufficiently dried compromising recovery and increasing apparent particle size due to aggregation in the collection vessel. The feed rate can be optimized for particular polymers, acids, bases salts and cargo. Mechanical parameters in the spray dryer can also be adjusted to further control particle size and aggregation.

The addition of surface-active compounds to the liquid feed such as BSA resulted in smaller particles with a narrower size distribution, likely due to improved drying kinetics. Particle size and shape can be further controlled by modifying the liquid feed formulation along with spray-drying parameters. Alginate gelation by single step spray drying was stable in aqueous suspensions. This was in contrast to non-cross-linked particles obtained with the same spray-drying parameters, which rapidly dissolved in the same aqueous solution.

About 65% of the encapsulated protein was released to the supernatant in aqueous suspensions of spray-dried particles obtained with the different formulations tested. Further incubation with a non-ionic surfactant and sonication did not increase the amount of protein released from these particles. This low protein recovery was possibly due to electrostatic interactions between the encapsulated protein and the negative charge in the alginates backbone and/or to the higher extent of cross-linking obtained by the internal gelation used in the method (in contrast to external gelation). Protein loss during spray drying could not be discarded. Furthermore, the addition of a hydrophobic polymer to the spraying formulations impacted the release rate of protein from the spray-dried particles, with higher latex concentrations resulting in a lower extent of protein release. This was possibly due to restricted water diffusion into the particles thereby limiting BSA release.

Additionally, a fast initial protein release rate was also observed. This was possibly due to the large pores generally associated to cross-linked alginates and/or to BSA being at the surface of the particles. BSA is a surface active protein that has been shown to partition to the air/water interface quite rapidly in spray drying experiments.

Accordingly, the present invention provides a method for microencapsulation of cargo compounds in a stable, cross-linked alginate matrix that results in small particle sizes and is easily scaled-up for industrial applications. The gentle gelation and moderate chemical environment used in the method will be useful for encapsulating a variety of bioactive compounds including cells, biopolymers and chemicals for many commercial applications, including in the food and pharmaceuticals industries. The methods are easily adapted to specific applications and can produce capsules with customized particle sizes and shapes as well as release kinetics.

From the discussion above it will be appreciated that the invention can be embodied in various ways, including the following:

1. A method of cross-linking polymer molecules, comprising: (a) mixing monomer molecules, at least one salt of an acid soluble multivalent ion and an acid neutralized with a volatile base; and (b) volatilizing said volatile base, thereby liberating said multivalent ions and initiating cross-linking of the monomer molecules.

2. The method as recited in embodiment 1, wherein the monomer is selected from the group of monomers consisting of alginates, polygalacturonates, chitosan, collagen, latex, soy proteins and whey proteins.

3. The method as recited in any of the previous embodiments, wherein the multivalent ion is a divalent cation.

4. The method as recited in any of the previous embodiments, wherein the divalent ion is selected from the group of ions consisting of barium ($Ba^{2+}$), calcium ($Ca^{2+}$), chromium ($Cr^{2+}$), copper ($Cu^{2+}$), iron ($Fe^{2+}$), magnesium ($Mg^{2+}$) and zinc ($Zn^{2+}$).

5. The method as recited in any of the previous embodiments, wherein the acid is an organic acid selected from the group of acids consisting of adipic acid, acrylic acid, glutaric acid, succinic acid, ascorbic acid, gallic acid and caffeic acid.

6. The method as recited in any of the previous embodiments, wherein the volatile base is selected from the group of volatile bases consisting of ammonia, methylamine, trimethylamine, ethylamine, diethylamine and triethylamine.

7. A method for producing microcapsules, comprising: (a) providing a formulation comprising: (i) monomer molecules; (ii) at least one acid neutralized with a volatile base; and (iii) an insoluble salt of a multivalent ion; (b) atomizing the formulation to form droplets; and (c) volatilizing the volatile base of the droplets, thereby lowering the pH of the formulation and making available said multivalent ion to cross-link the monomer molecules.

8. The method as recited in embodiment 7, further comprising adding a cargo to the formulation prior to atomization.

9. The method as recited in any of the previous embodiments, wherein the formulation further comprises a copolymer.

10. The method as recited in any of the previous embodiments, wherein the formulation further comprises a hydrophobic compound.

11. The method as recited in any of the previous embodiments, wherein the hydrophobic compound comprises latex.

12. The method as recited in any of the previous embodiments, wherein the monomer is selected from the group of monomers consisting of alginates, polygalacturonates, chitosan, collagen, latex, soy proteins and whey proteins.

13. The method as recited in any of the previous embodiments, wherein the salt is selected from the group of salts consisting of dicalcium phosphate, calcium carbonate, calcium oxalate, calcium phosphate, calcium meta-silicate and calcium tartrate.

14. The method as recited in any of the previous embodiments, wherein the acid is an organic acid selected from the group of acids consisting of adipic acid, acrylic acid, glutaric acid, succinic acid, ascorbic acid, gallic acid and caffeic acid.

15. The method as recited in any of the previous embodiments, wherein the volatile base is a base selected from the group of bases consisting of ammonia, methylamine, trimethylamine, ethylamine, diethylamine, and triethylamine.

16. A method for producing microcapsules, comprising: (a) providing a formulation comprising: (i) a plurality of at least one type of monomer molecule; (ii) citrate; (ii) at least one acid neutralized with a volatile base; (iii) a salt of an acid soluble multivalent ion; and (iv) a hydrophobic compound; (b) atomizing said formulation to form droplets; and (c) volatilizing the volatile base of the droplets, thereby lowering the pH of the formulation and making available the multivalent ion to cross-link the monomer molecules; wherein the hydrophobic compound modifies hydration properties of the dried particles to retard release of encapsulated compounds.

17. The method as recited in any of the previous embodiments, wherein the hydrophobic compound comprises a compound selected from the group of compounds comprising polymer latexes, wax emulsions and surfactants.

18. The method as recited in any of the previous embodiments, wherein the monomer is selected from the group of monomers consisting of alginates, polygalacturonates, chitosan, collagen, latex, soy proteins and whey proteins.

19. The method as recited in any of the previous embodiments, wherein the salt is selected from the group of salts consisting of dicalcium phosphate, calcium carbonate, calcium oxalate, calcium phosphate, calcium meta-silicate and calcium tartrate.

20. The method as recited in any of the previous embodiments, wherein the acid is an organic acid selected from the group of acids consisting of adipic acid, acrylic acid, glutaric acid, succinic acid, ascorbic acid, gallic acid and caffeic acid.

21. A method of cross-linking polymer molecules embodiment for use in spray drying applications to encapsulate biomolecules, cells and other chemical entities, comprising the steps of (a) providing a formulation comprising: (i) alginate polymer molecules; (ii) citric acid; (iii) adipic acid; (iv) ammonium hydroxide; and (v) dicalcium phosphate; (b) atomizing the formulation in a spray dryer; and (c) volatilizing the ammonia, as a result of the atomizing, thereby making calcium ions available for cross-linking the alginate polymer molecules.

22. A method of cross-linking polymer molecules embodiment for use in spray drying applications to encapsulate biomolecules, cells and other chemical entities, with control over the release rates of the encapsulated compounds, comprising the steps of (a) providing a formulation comprising: (i) alginate polymer molecules; (ii) citrate; (iii) succinic acid; (iv) ammonium hydroxide; (v) dicalcium phosphate; and (vi) hydrophobic compound; (b) atomizing the formulation in a spray dryer; and (c) volatilizing the ammonia, as a result of the atomizing, thereby making calcium ions available for cross-linking the alginate polymer molecules while modifying hydration properties of the dried particles to retard release of the encapsulated compounds.

23. A method of cross-linking polymer molecules embodiment for use in spray drying applications to encapsulate biomolecules, cells and other chemical entities, and control the release rates of encapsulated compounds, comprising the steps of (a) providing a formulation comprising: (i) alginate polymer molecules; (ii) citric acid; (iii) succinic acid; (iv) ammonium hydroxide; (v) dicalcium phosphate; and (vi) a latex polymer; (b) atomizing the formulation in a spray dryer; and (c) volatilizing the ammonia, as a result of the atomizing, thereby making calcium ions available for cross-linking the alginate polymer molecules while modifying hydration properties of the dried particles to retard release of the encapsulated compounds.

24. A method of cross-linking polymer molecules embodiment for use in spray drying applications to encapsulate biomolecules, cells and other chemical entities, and control over release rates of encapsulated compounds, comprising the steps of (a) providing a formulation comprising: (i) alginate polymer molecules; (ii) citrate; (iii) ascorbic acid; (iv) ammonium hydroxide; (v) dicalcium phosphate; and (vi) a latex polymer; (b) atomizing the formulation in a spray dryer; and (c) volatilizing the ammonia, as a result of the atomizing, thereby making calcium ions available for cross-linking the alginate polymer molecules while conferring anti-oxidative properties of the dried particles to protect oxygen-sensitive encapsulated compounds.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for."

TABLE 1

Examples Of Suitable Calcium Salts

| Chemical Name | Chemical Formula | Solubility in $H_2O$ (g/100 g) | Soluble in Acid? |
|---|---|---|---|
| Dicalcium phosphate | $CaH(PO_4)•2H_2O$ | 0.02 (24.5° C.) | yes |
| Calcium carbonate | $CaCO_3$ | 0.015 (25° C.) | yes |
| Calcium oxalate | $CaC_2O_4•H_2O$ | 0.0071 (25° C.) | yes |
| Calcium phosphate | $Ca(PO_4)_2$ | 0.002-0.003 (cold) | yes |
| Calcium meta-silicate | $CaSiO_3$ | 0.0095 (cold) | yes |
| Calcium tartrate | $CaC_4H_4O_6•4H_2O$ | 0.0032 (cold) | yes |

TABLE 2

Examples Of Acids That Can Be Used In This Invention

| Acid | $pK_a$ |
|---|---|
| Adipic | 4.43, 5.41 |
| Succinic | 4.16, 5.61 |
| Acrylic | 4.25 |
| Glutaric | 4.34, 5.41 |
| Ascorbic | 4.10, 11.6 |
| Gallic | 4.5, 10 |
| Caffeic | 4.62 |

TABLE 3

Spray-Dried Sample And Controls Described In Example 1

| Sample ID | Sample type | Description | Additional comments | Mass Recovery (%) |
|---|---|---|---|---|
| Control A | Non-cross-linked alginate | No acid was added to the solution prior to spraying, thus the $Ca^{2+}$ is never made available to cross-link. | Solution is easily pumped through nozzle. | 67 |
| Control B | Alginates cross-linked post-spraying through the nozzle | The pH is controlled as described. Cross-linking happens after spraying and during drying of the particles in the drying chamber. | Solution is easily pumped through nozzle. Exhaust vapor is at high pH, verifying that the ammonia is vaporized during the drying process. | 64-67 |
| Example 1 | Alginates plus enzyme cross-linked at the nozzle | Same as above, but with enzymes (cellulases and xylanases) in the solution with the encapsulation matrix. | Same comments as above. Enzymes are encapsulated in the alginate matrix. | 60-64 |

TABLE 3-continued Spray-Dried Sample And Controls Described In Example 1

| Sample ID | Sample type | Description | Additional comments | Mass Recovery (%) |
|---|---|---|---|---|
| Control C | Alginates cross-linked before spray-drying | The pH of the sample was not controlled in the manner described above and the availability of $Ca^{2+}$ for cross-linking was not controlled or limited. | This sample was mixed and sprayed quickly before cross-linking completely prevented spraying. The spraying nozzle was quickly clogged and yields were low. | 21 |

TABLE 4

Linear regression $R^2$-values and viscosities from FIG. 2

| Sample | Linear regression '$R^2$' | Viscosity ($\mu$)mPa*s |
|---|---|---|
| Control A | 0.999 | 5.53 |
| Control B | 0.992 | 1.13 |
| Example 1 | 0.856 | 1.80 |
| Control C | 0.995 | 1.11 |
| $H_2O$ | 0.986 | 0.75 |

TABLE 5

Size Distribution Of Spray-Dried Particles Measured By Mie Scattering In Oil

| | Particle size ($\mu$m) | | |
|---|---|---|---|
| Sample | d(0.1) | d(0.5) | d(0.9) |
| Control A | 2.808 | 7.372 | 23.695 |
| Control B | 8.079 | 37.092 | 218.932 |
| Example 1 | 6.146 | 22.884 | 76.529 |
| Control C | 4.848 | 19.234 | 69.314 |

TABLE 6

Compositions Of Typical Spray-dry Formulations

| Sample Type | Sample ID[†] | Formulation (%, w/v in $H_2O$) |
|---|---|---|
| Non cross-linked alginates | NCA | Alginate (2) |
| Cross-linked alginates | CA1 ± BSA | Alginate (1) $CaHPO_4 \cdot 2H_2O$ (0.1) Na-citrate (0.03) succinic acid[‡] (2) ± BSA (0.15) |
| Cross-linked alginates and latex | CA1L0.05 ± BSA | Alginate (1) $CaHPO_4 \cdot 2H_2O$ (0.1) Na-citrate (0.03) latex (0.05) succinic acid[‡] (2) ± BSA (0.15) |
| Cross-linked alginates and latex | CA1L0.25 ± BSA | Alginate (1) $CaHPO_4 \cdot 2H_2O$ (0.1) Na-citrate (0.03) latex (0.25) succinic acid[‡] (2) ± BSA (0.15) |
| Cross-linked alginates and latex | CA1L0.5 ± BSA | Alginate (1) $CaHPO_4 \cdot 2H_2O$ ((0.1) Na-citrate (0.03) latex (0.5) succinic acid[‡] (2) ± BSA (0.15) |
| Cross-linked alginates | CA2 ± BSA | Alginate (2) $CaHPO_4 \cdot 2H_2O$ (0.1) Na-citrate (0.03) succinic acid[‡] (2) ± BSA (0.15) |
| Non cross-linked Manugel | NCM | Manugel (2) |
| Cross-linked Manugel | CM ± BSA | Manugel (2) adipic acid[‡] (2) ± BSA (0.15) |
| Cross-linked Manugel | CM ± cellulase | Manugel (2) adipic acid[‡] (2) ± cellulase/xylanase mixture (0.048) |

[†]±BSA indicates that samples with and without bovine serum albumin were prepared.
[‡]Prepared separately by dissolving in water and adjusting pH > $pK_a$ of the organic acid (≈5.6) with ammonium hydroxide.

We claim:

1. A method of cross-linking polymer molecules, comprising:
    (a) mixing monomer molecules, at least one salt of an acid soluble multivalent ion and an acid neutralized with a volatile base; and
    (b) volatilizing said volatile base, thereby liberating said multivalent ions and initiating cross-linking of the monomer molecules.

2. The method of claim 1, wherein said monomer is selected from the group of monomers consisting of alginates, polygalacturonates, chitosan, collagen, latex, soy proteins and whey proteins.

3. The method of claim 1, wherein said multivalent ion is a divalent cation.

4. The method of claim 3, wherein said divalent cation is selected from the group of cations consisting of barium ($Ba^{2+}$), calcium ($Ca^{2+}$), chromium ($Cr^{2+}$), copper ($Cu^{2+}$), iron ($Fe^{2+}$), magnesium ($Mg^{2+}$) and zinc ($Zn^{2+}$).

5. The method of claim 1, wherein said acid is an organic acid selected from the group of acids consisting of adipic acid, acrylic acid, glutaric acid, succinic acid, ascorbic acid, gallic acid and caffeic acid.

6. The method of claim 1, wherein said volatile base is selected from the group of volatile bases consisting of ammonia, methylamine, trimethylamine, ethylamine, diethylamine and triethylamine.

7. A method of cross-linking polymer molecules, comprising:
    (a) mixing polymer molecules, at least one salt of an acid soluble multivalent ion and an acid neutralized with a volatile base; and
    (b) volatilizing said volatile base, thereby liberating said multivalent ions and initiating cross-linking of the polymer molecules.

* * * * *